United States Patent [19]

Naggi et al.

[11] Patent Number: 4,727,063
[45] Date of Patent: Feb. 23, 1988

[54] DEPOLYMERIZED AND SUPERSULFATED HEPARIN, PROCESS FOR ITS PREPARATION AND PHARMACEUTICAL COMPOSITIONS

[75] Inventors: Annamaria Naggi, Legnano; Giangiacomo Torri, Bergamo, both of Italy

[73] Assignee: Sclavo, Siena, Italy

[21] Appl. No.: 737,496

[22] Filed: May 24, 1985

Related U.S. Application Data

[63] Continuation-in-part of Ser. No. 565,604, Dec. 27, 1983, abandoned.

[30] Foreign Application Priority Data

Dec. 28, 1982 [FR] France ................... 82 21934

[51] Int. Cl.$^4$ .............. A61K 31/725; C08B 37/10
[52] U.S. Cl. .................................. 514/56; 536/21; 514/822
[58] Field of Search ............... 514/56, 822; 536/21, 536/20, 22, 33, 56

[56] References Cited

U.S. PATENT DOCUMENTS

| | | | |
|---|---|---|---|
| 2,697,093 | 12/1954 | Jones | 536/59 |
| 3,578,657 | 5/1971 | Ricard et al. | 536/112 |
| 3,951,949 | 4/1976 | Hamuro et al. | 260/233.3 R |
| 4,266,077 | 5/1977 | Conrow et al. | 562/427 |
| 4,281,168 | 7/1981 | Fussi | 536/21 |
| 4,303,651 | 12/1981 | Lindahl et al. | 514/56 |

FOREIGN PATENT DOCUMENTS

| | | | |
|---|---|---|---|
| 0240037 | 3/1979 | France | 514/56 |
| 2474508 | 7/1981 | France | 514/56 |
| 2002406 | 2/1979 | United Kingdom | 536/21 |

OTHER PUBLICATIONS

Vinazzer et al., Thrombosis Res., 27: 341–352, 1982.
Fitzgerald et al., Chem., Abst., 67: 62716e, 1967.
Yamada et al., Chem. Abst., 55: 26236b, 1961.
Cifonelli, Chem. Abst., 82: 68076c, 1974.
Cifonelli, Chem. Abst., 84: 159537m, 1976.
Roubal et al., Chem. Abst., 56: 5348d, 1962.
Nagasawa et al., Chem. Abst., 76: 113456v, 1972.
Chugia, Chem. Abst., 58: 11176b, 1962.

Primary Examiner—J. R. Brown
Assistant Examiner—John W. Rollins
Attorney, Agent, or Firm—Stevens, Davis, Miller & Mosher

[57] ABSTRACT

Novel depolymerized and supersulfated heparin having a molecular weight comprised between 2000 and 9000 and a sulfation degree of at least 2.5, in which all of the primary hydroxy groups are sulfated; a process for its preparation by reacting a heparin of natural origin, or a fraction thereof with a sulfuric acid/chlorosulfonic acid mixture; and pharmaceutical compositions containing it as active ingredient, having potential antithrombotic, hypolipemic and fibrinolytic activity and useful in the prevention of thrombosis and for the treatment of atherosclerosis.

17 Claims, 10 Drawing Figures

DEPOLYMERIZED AND SUPERSULFATED HEPARIN, PROCESS FOR ITS PREPARATION AND PHARMACEUTICAL COMPOSITIONS

CROSS REFERENCE TO RELATED APPLICATION

This is a continuation-in-part of the application Ser. No. 565,604 filed on Dec. 27, 1983, now abandoned.

FIELD OF THE INVENTION

The present invention concerns a depolymerized and supersulfated heparin, a process for its preparation and pharmaceutical compositions containing it as active ingredient.

BACKGROUND OF THE INVENTION

Heparins are polysaccharides widely distributed in animal tissues. As a result of an incomplete biosynthesis, heparins have hybrid structures which can be statistically represented by "average" disaccharide repeating units intermediate between the non-sulfated units of the precursor (A)

and the trisulfate units (B)

It is understood that heparin is not a single molecule represented by an intermediate structure between the (A) and the (B) ones having n disaccharide units. It is a population of molecules all having an intermediate structure between the (A) and the (B) ones having a very variable value of n as specified hereinbelow.

Practically, heparin is a polysaccharide composed of molecules of glucuronic acid and iduronic acid largely sulfated in 2-position, linked to molecules of glucosamine largely sulfated in 6-position and sulfated or acetylated on the amine in 2-position.

The structure of heparin may be statistically represented by the following formula wherein A represents H and $SO_3^-$, B represents $SO_3^-$ and $COCH_3$ and n is an integer from 20 to 30.

The expression "n is an integer from 20 to 30" means that most of the heparin molecules is represented by the structure I above, where the disaccharide unit is repeated from 20 to 30 times, which corresponds to a molecular weight of from 12000 to 18000.

The expressions "H and $SO_3^-$" and "$SD_3^-$ and $COCH_3$", as used herein for the substituents A and B, respectively, indicate that in the above 20 to 30 disaccharide units A is in some cases hydrogen and in other cases a $SO_3^-$ group and, analogously, B in most of cases is $SO_3^-$ and in other cases is an acetyl group.

Likewise, the bond ⟨ , as herein drawn, indicates that the $COO^-$ group, in some of the 20 to 30 disaccharide units has the configuration of the D-glucuronic acid and in most of said n units has the configuration of the L-iduronic acid.

Heparin possesses a good antithrombotic activity and, therefore, it is used particularly in the prevention of postoperative deep venous thrombosis. However, the antithrombotic activity of heparin is broadly ascribed to its anticoagulant action and, therefore, it causes the physician serious problems of monitoring because of the high risk for hemorrhage associated with heparin therapy.

The structure and the properties of heparins are summarized in a paper by B. Casu et al. (Arzneimittel-Forschung 1983, 33, 135–142) which shows that the hydroxy groups in the position 3 of the glucosamine and of the iduronic or glucuronic acids subunits are not sulfated, even though minor amounts of 3-O-sulfate groups, not exceeding 1% (U. Lindhal et al., Proc. Natl. Acad. Sci. USA 1980, 77, 6551–6555; B. Casu et al., Biochem. J. 1981, 197, 599–609), have been detected. The above Casu et al. paper describes a series of natural heparins having a very large spectrum of sulfation degree which, in the case of a highly purified beef lung heparin, reaches 2.55, namely the highest sulfation degree never found in a heparin, showing that such a heparin is rich in structures (B) above.

Polysaccharides other than heparin have been sulfated and transformed into the so-called "heparinoids" which are active on the coagulation system. The polyxylan sulfate, also named SP-54, having the structure where R is SO$_3$NA or H, is used as a therapeutically active agent, but it is chemically different from heparin. More particularly, polyxylan sulfate has not any primary hydroxy group nor any N-sulfate group.

DESCRIPTION OF THE PRIOR ART

Heparins or fractions or fragments thereof having a sulfation degree higher than that of the natural heparins have never been described. Moreover, heparins or fractions or fragment thereof substantially sulfated in the 3 position of the glucosamine subunit have never been described.

It is known in literature that by depolymerizing heparin to low molecular weight heparins (as "low molecular weight heparins" are herein designated depolymerized heparins having a molecular weight in the range of from 2000 to 9000), compounds having practically the same antithrombotic activity but a reduced anticoagulant effect (Seminars in Hematology 1978, 15, 1–17) are obtained.

It is also generally recognized that at the same degree of polymerization, the biological activity of polysaccharides increases with their sulfation degree.

The term "sulfation degree" in the case of heparin and, generally, of the other glucosaminoglycanes, designates the number of sulfate groups (SO$_3^-$) per disaccharide unit I above. Pure commercial heparins, generally obtained from pig intestinal mucosa have a sulfation degree comprised between 1.8 and 2.3, generally about 2. The sulfation degree is also expressed by the ratio SO$_3^-$/COO$^-$.

Many processes for the depolymerization of heparin and the consequent preparation of low molecular weight heparins have been described in the literature.

The published European patent application No. 37 318 and the International patent application No. 81,00 519 describe a deaminative cleavage with nitrous acid. This process involves the formation of a depolymerized heparin bearing, at the end of the chain, an aldehyde having the skeleton

II

The published European patent application No. 40 144 describes a process of basic hydrolysis which, by beta elimination, affords depolymerized heparins bearing, at the end of the chain, an unsaturated sugar having the skeleton

III

The published French patent application No. 2 474 508 describes an acid hydrolysis carried out with ascorbic acid and hydrogen peroxide which leads to depolymerized heparins having lost the SO$_3^-$ group in 2-position of glucosamine which is responsible for the biological activity. Therefore, the product thus obtained must be N-sulfated again to recover its activity.

Another known process for depolymerizing heparin (J. Biol. Chem. 1982, 257, 7310–7313) concerns an enzymatic hydrolysis, which leads to a product which, at an end of its chain, has the insaturated sugar III above and which has lost 90% of its activity.

Other low molecular weight heparins have been heretofore described.

In the U.S. Pat. No. 4,303,651 there are disclosed heparin fragments having 14–18 sugar units in which the main structural components, i.e. the L-idurosonyl-2-O-sulfate-(1-alpha-4)-N-sulfo-D-glucosamine-6-O-sulfate as the dominating saccharide unit, are the same as in standard heparin. However, these heparin fragments are not supersulfated because they are obtained by fractionation of depolymerized natural heparins without any sulfation. On the contrary, in these heparin fragments the amount of nonsulfated iduronic acid residues is considerably higher than in the starting material because these residues are part of sequences concentrated by the affinity chromatography on antithrombin used in the process. Moreover, in the same fragments, N-acetylglucosamine is in sulfated and unsulfated form on the 6-hydroxy group.

In U.S. Pat. No. 4,281,108 there are described reconstituted depolymerized heparins obtained by acidification of heparin to form heparinic acid, depolymerization of said heparinic acid in the presence of peroxides to form a low molecular weight heparamine and sulfation of said heparamine to form the corresponding low molecular weight heparin. This process involves the hydrolysis and the reconstitution of the N-sulfate group of the starting heparin only. The compounds thus obtained are not supersulfated because the method used for resulfation purposes is essentially selective for the amino group and does not affect the hydroxy groups.

British patent specification No. 2,002,406 discloses oligo-hetero-polysaccharides containing the sulfuric groups "in the quantities and the positions which are characteristic of the heparin molecule" obtained by sulfation of hyposulfated heparin fractions using pyridine sulfotrioxide.

In summary, literature does not disclose any heparin or fraction or fragment thereof having sulfate groups in quantities superior to that of the natural heparins.

SUMMARY OF THE INVENTION

It has now been found that by treating heparin with a mixture of sulfuric acid and chlorosulfonic acid a depolymerized heparin having a molecular weight between 2000 and 9000 is obtained in good yields.

It has also surprisingly been found that the depolymerized heparin thus prepared possesses a sulfation degree at least 20% higher than that of the starting heparin. This novel heparin is herein designated "supersulfated" and is characterized by the dominating tetrasulfated disaccharide unit (C)

It has further been found that in the depolymerized and supersulfated heparin thus obtained the primary hydroxy groups at the 6-position of all the glucosamine subunits are esterified by a sulfate group and that at least the hydroxy group in the 3-position of the glucosamine residue of the disaccharide units is extensively sulfated.

This finding is really very surprising because heparin is a very sensitive molecule which undergoes an extensive degradation by treatment with sulfuric acid alone whilst it does not undergo any substantial sulfation on its hydroxy groups by treatment with chlorosulfonic acid in pyridine according to the known method used to introduce a sulfate group on the amino group of the glucosamine subunit.

It has finally been found that the new depolymerized and supersulfated heparin shows a good fibrinolytic and hypolipemic activity joined to a weak anticoagulant activity.

Thus, it is an object of the present invention to provide a novel depolymerized and supersulfated heparin having a molecular weight comprised between 2000 and 9000 and a sulfation degree at least 20% higher than that of the corresponding heparin.

This increase in the sulfation degree is given in percent because the commercial heparins have a sulfation degree depending upon the sources and the extraction and/or purification process.

Anyhow, the sulfation degree of the novel depolymerized and supersulfated heparin of the present invention is at least 2.5, namely higher than that of all the known heparins obtained from pig intestinal mucosa and of all low molecular weight heparins heretofore described.

The novel depolymerized and supersulfated heparin of the present invention is characterized by a structure represented by the following formula wherein A and B are as hereinabove defined and m is an integer from 4 to 15.

As for formula I above, the expressions "H and $SO_3^-$" and "$SO_3^-$ and $COCH_3$" utilized for A and B, respectively, as well as m and the bond ⌇ illustrate the statistical character of formula IV.

More particularly, in the formula IV
m is as defined above;
B is a $COCH_3$ group in 0 to about 30% of the m disaccharide units, according to the percent of acetyl group existing in the commercial heparin from which the supersulfated heparin derives, and a $SO_3^-$ group in the remaining disaccharide units;
the substituent A in the position 3 of the glucosamine subunit is $SO_3^-$ in at least 30% of the m disaccharide units and hydrogen in the remaining ones;
the substituent A in the position 2 of the uronic acid subunit is $SO_3^-$ in at least 50% of the m disaccharide units and hydrogen in the remaining ones;
the substituent A in the position 3 of the uronic acid subunit is prevalently hydrogen, but it can be $SO_3^-$ in some of the m disaccharide units.

Preferred depolymerized, supersulfated heparins according to the present invention are those of formula IV above, in which
m is as defined hereinabove;
B is a $COCH_3$ group in 0 to about 30% of the m disaccharide units, according to the percent of acetyl groups existing in the commercial heparin from which the supersulfated heparin derives, and a $SO_3^-$ group in the remaining disaccharide units;
the substituent A in the position 3 of the glucosamine subunit is $SO_3^-$ in at least 50% of the m disaccharide units and hydrogen in the remaining ones;
the substituent A in the position 2 of the uronic acid subunit is $SO_3^-$ in at least 70% of the m disaccharide units and hydrogen in the remaining ones;
the substituent A in the position 3 of the uronic acid subunit is prevalently hydrogen, but it can be $SO_3^-$ in some of the m disaccharide units.

Particularly preferred is a depolymerized and supersulfated heparin of formula IV above, in which m is as hereinabove defined, having a sulfation degree of from $3.0 \pm 0.1$ to $3.3 \pm 0.1$.

In formulas I and IV above, as well as in the claims, the products are indicated in anionic form. Cation may be hydrogen, an alkaline metal, preferably sodium, or an alkaline-earth metal, preferably calcium or an organic physiologically compatible amine.

It is another object of the present invention to provide a process for the preparation of a depolymerized and supersulfated heparin having a molecular weight of from 2000 to 9000, represented more particularly by the formula IV above, and of its pharmaceutically acceptables salts, in which a heparin of natural origin or a fraction thereof is treated with a mixture of sulfuric acid and chlorosulfonic acid and the product thus obtained is isolated as an alkali metal salt or transformed in the acid form or in another pharmaceutically acceptable salt.

In the mixture, the two acids are concentrated; preferably their concentration is at least 95% by weight.

It is understood that a concentration referred to sulfuric acid involves the presence of water; generally chlorosulfonic acid is 100%, but a percent of impurities, like sulfur trioxide may be contained therein. Anyhow, when sulfuric acid and chlorosulfonic acid are mixed, the water contained in sulfuric acid is destroyed by the chlorosulfonic acid.

The ratio of the two acids is highly variable; a ratio sulfuric acid:chlorosulfonic acid of about 2:1 is particularly preferred, but such a ratio can vary from 4:1 to 1:4.

The reaction temperature may vary from $-20°$ to $+40°$ C.

The presence of water in the reaction medium is critical; more particularly, water regulates the hydrolysis of the polysaccharide chains and influences the molecular weight of the depolymerized, supersulfated heparins to be obtained.

Normally, the moisture absorbed from the atmosphere is sufficient to hydrolyze the starting heparin.

The reaction is carried out by introducing heparin in the mixture of the two acids; after a period varying from some minutes to 2 hours, according to the reaction temperature, the desired depolymerization is complete and the low molecular weight, supersulfated heparin is isolated in the form of an alkaline salt in aqueous solution by precipitation with an appropriate solvent, such as diethyl or diisopropyl ether, dissolution in water, neutralization with an alkaline, preferably sodium, hydroxide or carbonate, and final dialysis to eliminate the smallest fragments.

According to the process of the present invention, it is possible to regulate the degree of polymerization and to obtain depolymerized, supersulfated heparins by varying in a suitable manner the amount of water, with or without taking into consideration the environmental water.

For example, it is possible to operate in an anhydrous medium and to add the suitable amount of water. It has been found that the best results are obtained by adding diluted sulfuric acid, for example 70–85% v/v sulfuric acid, to the reaction medium.

According to a preferred embodiment, the process of the present invention is carried out by mixing 95–98% sulfuric acid and chlorosulfonic acid at a temperature below $-3°$ C. and, when the development of gas has practically ceased, the starting heparin, as anhydrified as possible, is added to the acids mixture. Then, diluted sulfuric acid is added in an amount of from about 0.2 to about 1.5 g of sulfuric acid per gram of starting heparin. Practically, by using, for example, 80% v/v sulfuric acid, 1 to 5 ml of such acid per gram of the starting heparin are added to the reaction mixture. After one hour at the temperature below $-3°$ C., the mixture is allowed to reach room temperature spontaneously and the depolymerized, supersulfated heparin is then isolated.

Generally, the whole process lasts 2–2.5 hours.

The depolymerized and supersulfated heparin is isolated in the form of alkaline salt according to conventional techniques, for example by lyophilisation or by evaporation under reduced pressure, and characterized according to the known physicochemical methods.

Other salts, such as the calcium salt, may be obtained starting from alkaline salts, sodium salt preferably, by exchange reaction with the appropriate salt, for example a calcium salt, by optionally utilizing an ion exchange resin.

If desired, the final solution containing the depolymerized and supersulfated heparins can be submitted to an ultrafiltration in order to separate different families of fragments having the desired molecular weight.

For example, by submitting the solution containing the whole depolymerized and supersulfated heparin to an ultrafiltration using a porous filter (G3) having a molecular cut off of 1000, there is obtained two fractions: one containing fragments of depolymerized and supersulfated heparin having a molecular weight lower than 5000 and the other containing supersulfated fragments having a molecular weight higher than 5000.

The physicochemical methods used have shown that the novel depolymerized and supersulfated heparins of the present invention differ qualitatively from the corresponding heparins and from all the known depolymerized heparins because, with an equal degree of polymerization, their sulfation pattern is significantly different owing to the additional sulfate groups.

Such a difference is evidenced both by the electrophoretic pattern and by the NMR spectrum characteristics.

According to the technique of barium acetate electrophoresis, the migration of the sulfated species is inversely proportional to their capability of complexing $Ba++$ ions. This complexing capability is function of the molecular weight as well as of the charge density.

In the case of non modified heparin, the chains having a stronger affinity for barium stop ("slow moving" species) whereas the others migrate towards the anode ("fast moving" species).

In the case of the known depolymerized heparins, the "fast moving" species only are observed.

On the contrary, differently from natural heparins, the novel depolymerized and supersulfated heparins of the present invention show "slow moving" species only.

NMR spectra confirm the qualitative difference between the commercial heparins or the known depolymerized heparins (whose spectra are substantially identical, except for the signals of the terminal groups) and the depolymerized and supersulfated heparins of the present invention. Actually, NMR spectra of the compounds of the invention exhibit significant displacements of the signals which may be attributed to the new sulfate groups introduced into the positions which generally are not sulfated. Such NMR spectra justify the formula IV above.

The process of the present invention may be carried out not only on commercial heparins, but also on fractions of such heparins.

According to the process of the present invention, depolymerization takes place under conditions which do not induce structural variation in saccharide units, i.e. formation of unsaturated or aldehyde products and which practically do not cause decarboxylation.

According to the process of the present invention, very homogeneous depolymerized, supersulfated heparins are obtained even starting from different preparations of heparins. Very likely, the same depolymerized, supersulfated heparins can be obtained from heparins of different origin. This property makes the process of the present invention unique in respect of all the known processes.

The novel depolymerized and supersulfated heparins of the present invention have been assayed in rats in the blood coagulation, fibrinolysis and circulating lipoprotein lipase activity tests.

The action of the compounds of the present invention on the blood coagulation has been quantitized by the ratio of the activity towards the factor Xa (anti-Xa activity) and the activity on the extrinsic total coagulation (APTT; Activated Partial Thromboplastin Time).

Factor Xa is the enzyme responsible for the transformation of prothrombin into thrombin; therefore, anti-Xa action prevents the formation of circulating thrombin. The action on APTT comprises all the effects towards the whole coagulation factors participating to the extrinsic pathway, thrombin included, therefore it is considered as an indirect measure of the hemorragic risk, particularly under heparin therapy.

Accordingly, the ratio anti-Xa/APTT allows to evaluate the anticoagulant component of the potential antithrombotic activity of the depolymerized and supersulfated heparins of the present invention without associated hemorragic risks.

The other component of this potential antithrombotic activity is fibrinolysis.

The hypolipemic activity of the compounds of the present invention was determined by evaluating their action on lipoprotein lipase which allows to accelerate triglycerides catabolism.

Three representative compounds of the present invention, the depolymerized and supersulfated heparins designated by their codes AH-16 (Example 1), AH-17 (Example 4) and AH-19 (Example 3) respectively, as well as a starting heparin (D-212/A) of Example 4) as reference compound, were given to rats in a single intravenous dose of 50 IU/kg (0.3 mg/kg) and the different biological parameters were determined 15 minutes after the administration of the products. The action on whole blood coagulation was determined on citrated plasma samples according to conventional techniques (R. R. Proctor and S. I. Rapaporti, Am. J. Clin. Pathol., 1961, 36, 212). The same samples were utilized to determinate the anti-Xa activity according to a chronometric dosage (E. T. Yin, S. Wessler, J. V. Butler, J. Lab. Clin. Med. 1973, 81, 298-310).

Table I summarizes the influence of the compounds of the present invention on blood coagulation, in comparison with a starting heparin.

TABLE I

| PRODUCT | DOSE IU/kg i.v. | APTT U/ml | ANTI-Xa U/ml Chronometric | ANTI-Xa/ APTT |
|---|---|---|---|---|
| AH-16 | 50 | 0.06 ± 0.02 | 0.18 ± 0.01 | 3 |
| AH-17 | 50 | 0.05 ± 0.02 | 0.17 ± 0.01 | 3.4 |
| AH-19 | 50 | 0.05 ± 0.03 | 0.22 ± 0.04 | 4.4 |
| D-212/A | 50 | 0.212 ± 0.04 | 0.324 ± 0.04 | 1.61 |

In another assay two samples of depolymerized and supersulfated heparins of the present invention, AH-104 (Example 6) and AH-106 (Example 9) were compared, according to the method described above, to the starting heparin D-212 of Examples 1, 3 and 5 to 10. The products were administered at the dose of 125 IU/kg (0.75 mg/kg).

Results are recorded in Table II.

TABLE II

| PRODUCT | DOSE IU/kg i.v. | APTT U/ml | ANTI-Xa U/ml Chronometric | ANTI-Xa/ APTT |
|---|---|---|---|---|
| AH-104 | 125 | 0.078 ± 0.007 | 0.30 ± 0.03 | 3.84 |
| AH-106 | 125 | 0.080 ± 0.007 | 0.31 ± 0.05 | 3.87 |
| D-212 | 125 | 1.000 ± 0.090 | 1.20 ± 0.04 | 1.20 |

It results from Tables I and II that samples AH-104 and AH-106, which are identical, are more active towards factor Xa (anti-Xa activity) that on the whole coagulation. Their Anti-Xa/APTT ratio is at least twice as high as that of reference heparins D-212/A and D-212.

The fibrinolytic activity was assessed by evaluating the lysis area induced by plasma euglobulins on fibrin plaques (C. Kluft, Haemostasis, 1976, 5, 136). In this case, the i.v. administered dose was 0.75 mg/kg.

The lipoprotein lipase activity was assessed by the capability of hydrolysing the 14C-triolein substrate into 14C-oleic acid according to the technique of Nikkola and coll. (Metabolism 1977, 26, (2), 179).

Table III summarizes the ex-vivo action of a compound of the present invention, AH-16, on fibrinolysis and lipoprotein lipase, compared with the starting heparin D-212.

TABLE III

| PRODUCT | FIBRINOLYSIS (a) lysis area | LIPOPROTEINE LIPASE (b) release % |
|---|---|---|
| AH-16 | 304.26 mm2 ± 12.63 (*) | 95* |
| D-212 | 272.83 mm2 ± 15.43 (**) | 28 |

(a) *$p < 0.01$ **$p < 0.05$ Test of Duncan;administered dose 0.75 mg/kg, i.e. 125 IU/kg
(b) Statistical analysis: test of Student in comparison with heparin
*$p < 0.01$ It results from this Table that a statistically significant increase of the lysis area on the fibrin plaque was obtained in the case of sample of plasma euglobulins from animals treated with standard heparin (D-212). Such increase was actually more pronounced in animals treated with the depolymerized and supersulfated heparin (AH-16).

Besides, the results obtained on lipoprotein lipase prove that the compound of the invention has a significant activity which is about three times higher than that of heparin D-212, whose activity is not significant.

Thus depolymerized and supersulfated heparins of the present invention are not only potential antithrombotics without associated hemorragic risks, but also potential hypolipemic agents.

Thus, it is another object of the present invention to provide pharmaceutical compositions containing, as active ingredient, a depolymerized and supersulfated heparin of formula IV above.

In the pharmaceutical compositions of the present invention for oral, sublingual, sub-cutaneous, intramuscular, intravenous, transdermic or rectal administration, the active ingredients of formula IV above may be administered in dosage unit form, in admixture with conventional pharmaceutical carriers, to animals and human beings in cases of pathologic rise of thrombin and lipids, particularly for the prevention of thrombotic diseases and the treatment of atherosclerosis. Appropriate dosage unit forms include forms for oral administration such as tablets, capsules, powders, granules and oral solutions or suspensions and forms for parenteral administration useful for subcutaneous intramuscular or intravenous injection.

In order to obtain the antithrombotic and hypolipemic effect in mammals and human the daily dose of active ingredient may vary between 0.1 and 100 mg per kg of body-weight.

Each unit dose may contain from 1 to 1500 mg of active ingredient in admixture with a pharmaceutical carrier.

This unit dose may be administered from 1 to 4 times daily to treat troubles of lipid metabolism and generally to treat atherosclerosis.

The following examples illustrate the invention without, however, limiting it.

EXAMPLE 1

To a mixture of 20 ml of 95% sulfuric acid and 10 ml of chlorosulfonic acid, cooled to a temperature between $-4°$ and $0°$ C., there is added 1 g of heparin from pig intestinal mucosa (PROQUIFIN, lot 7926-7935, code number: D-212) having a sulfation degree of 1.95 and a molecular weight 13500, then it is stirred for 1 hour at the same temperature. After further 60 minutes at room temperature, the mixture is poured into 500 ml of cold diethyl ether ($-4°$ to $4°$ C.), the precipitate is filtered and washed with cold diethyl ether. The product thus obtained is dissolved in water, neutralized with 0.5N sodium hydroxide and dialysed against distilled water in membranes at 3500 D (THOMAS DIALYZER TUBING 3787-H47, 11 mm diameter). Thus a desalting is obtained as well as the elimination of low molecular fragments. By slow evaporation under reduced pressure, a depolymerized and supersulfated sodium heparin (code number: AH-16) is obtained in 93% yield by weight, as a powder having the following characteristics:

M.W.: about 6000 (formula IV, m about 9), calculated from elution volume in gel chromatography on Sephadex G-75 calibrated with heparin standard samples of known molecular weight;

Elemental analysis: S: 12.93%; C: 18.48%; H: 3.30%; N: 1.76%

Sulfation degree ($SO_3^-/COO^-$): 3.0

Figure 1:
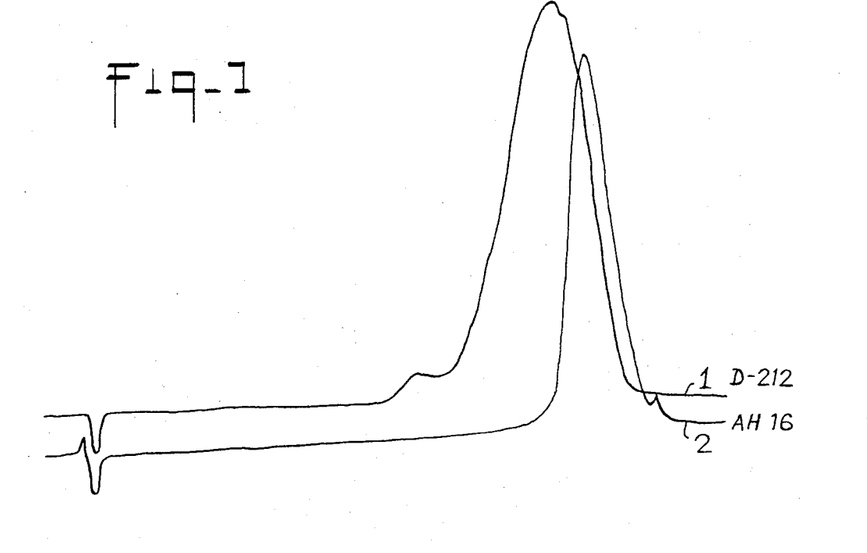

IR spectrum: broad band in the region 1300-1200 $cm^{-1}$, characteristic of the sulfate groups Electrophoresis in hydrochloric acid: with this technique, the migration is function of the sulfation degree. FIG. 1 shows the significant increasing of the electrophoretic migration of the depolymerized and supersulfated heparin compared with the starting heparin.

Figure 2:
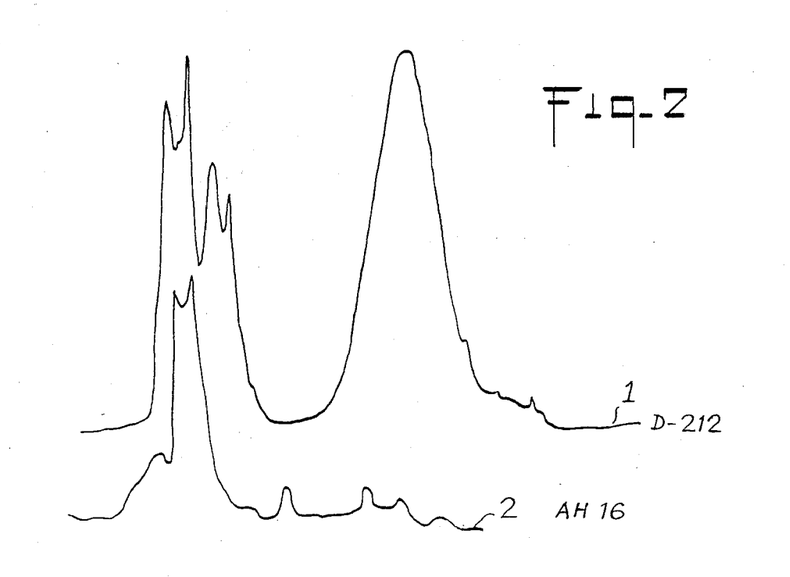

Barium acetate electrophoresis: FIG. 2 shows that depolymerized and supersulfated heparin has a "slow-moving" electrophoretic characteristic, differently from the starting heparin containing both "slow-moving" and "fast moving" components.

Figure 3:
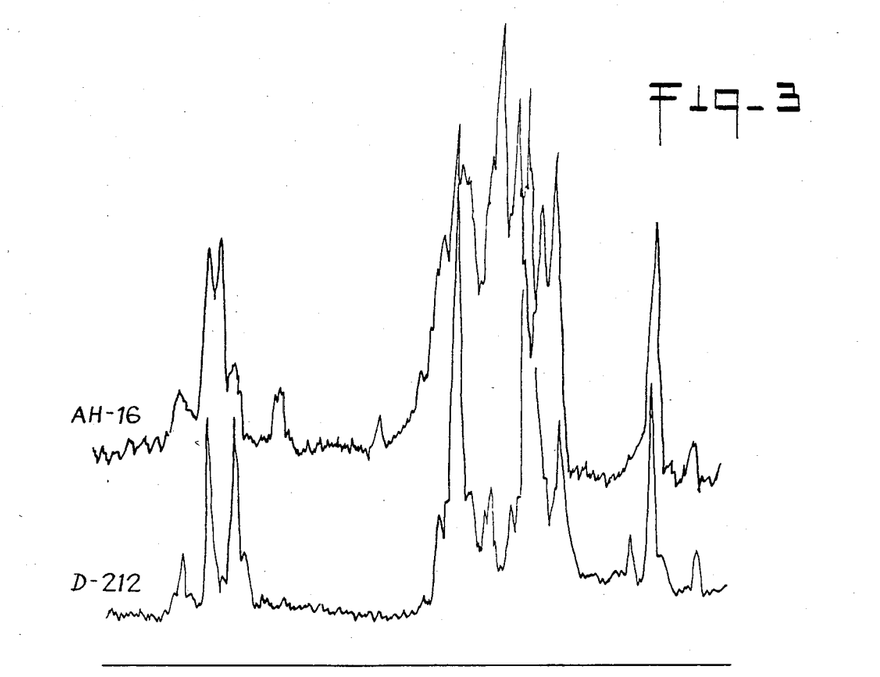

13C-NMR spectrum: FIG. 3 shows the comparison between the spectrum of the starting heparin and that of depolymerized and supersulfated heparin. In the spectrum of the new, low molecular weight heparin new signals appear, due to the effect of the depolymerisation and of the introduction of additional sulfate groups. The disappearance of the 6-OH signal is also noted. The depolymerized and supersulfated heparin thus obtained shows a sulfation degree which is 53% higher than that of starting heparin without any significant decarboxylation.

EXAMPLE 2

To a mixture of 10 ml of 98% sulfuric acid and 5 ml of chlorosulfonic acid, cooled to a temperature between $-4°$ and $0°$ C., there are added 500 mg of an high molecular weight fraction (M.W. 16500, code number: D-212/B), obtained by precipitation with ethanol and having a sulfation degree ($SO_3^-/COO^-$) of 2, of heparin PROQUIFIN, lot 7926-7935. The mixture is left to stand 1 hour at room temperature, then it is poured into 250 ml of cold diethyl ether ($-10°$ to $4°$ C.) and filtered; the precipitate thus obtained is dissolved in water, the solution is neutralized with 0.5N sodium hydroxide and dialysed against distilled water in membranes at 3500 D (THOMAS DIALYZER TUBING 3787-H47, 11 mm diameter), in order to eliminate the salts and the smallest size reaction products. By evaporation under reduced pressure, a depolymerized and supersulfated sodium heparin (code number: AH-18) is obtained in 60% yield. The product has the following characteristics:

M.W.: 3000-5000 (formula IV, m=5-8)

Elemental analysis: S: 13.56%; C: 18.03%; H: 3.00%; N: 1.70%

Sulfation degree ($SO_3^-/COO^-$): 2.6

Figure 4:
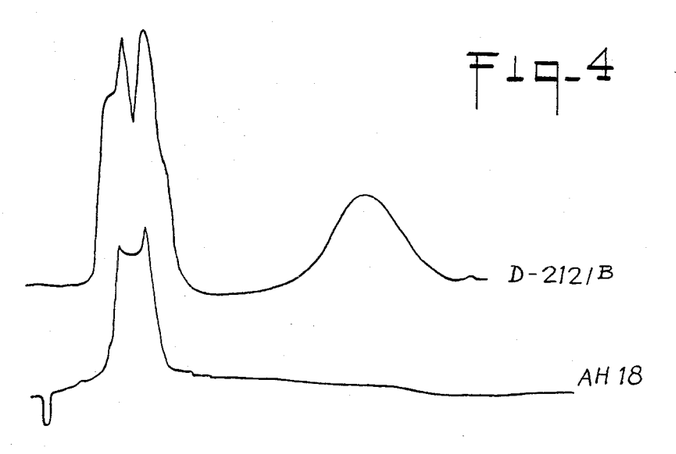

IR spectrum: broad band in the region 1300-1200 $cm^{-1}$, characteristic of the sulfate groups Barium acetate electrophoresis: FIG. 4 indicates that AH-18 shows "slow-moving" components only, whereas the starting roduct also shows "fast-moving" components.

EXAMPLE 3

To a mixture of 10 ml of 98% sulfuric acid and 5 ml of chlorosulfonic acid, cooled to a temperature between $-4°$ and $0°$ C., there are added 500 mg of sodium heparin from pig intestinal mucosa (PROQUIFIN, lot 7926-7935, code number: D-212) having sulfation degree ($SO_3^-/COO^-$) of 1.95. The mixture is left to stand 1 hour at room temperature, then it is poured into 250 ml of cold diethyl ether ($-10°$ to $4°$ C.), and afterwards treated as described in Examples 1 and 2. Thus, a depolymerized and supersulfated sodium heparin (code number: AH-19) is obtained in 90% yield. The product has the following characteristics:

M.W.: about 6000 (formula IV, m=about 9)

Sulfation degree ($SO_3^-/COO^-$): 3.0

Figure 5:
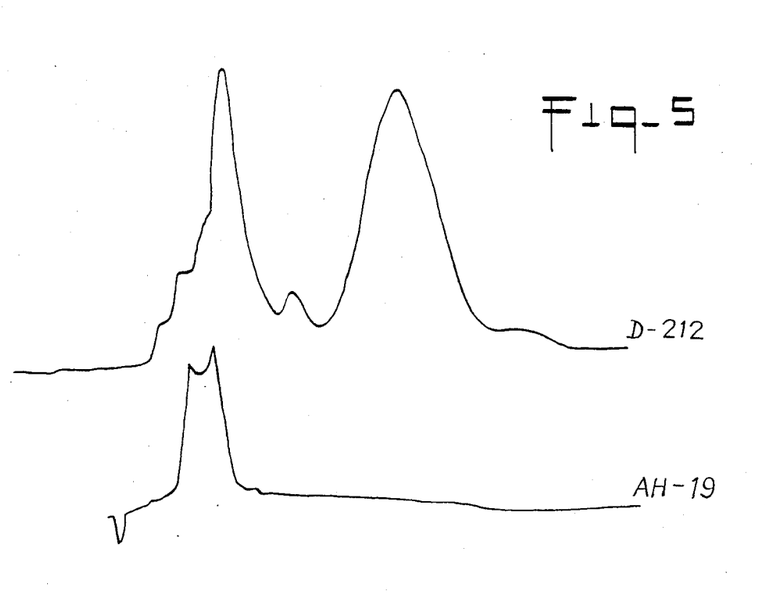

IR spectrum: broad band in the region 1300-1200 $cm^{-1}$, characteristic of the sulfate groups Barium acetate electrophoresis: FIG. 5 indicates that AH-19 shows "slow-moving" components only, whereas the starting product also shows "fast moving" components.

EXAMPLE 4

To a mixture of 10 ml of 98% sulfuric acid and 5 ml of 95% chlorosulfonic acid, cooled to a temperature between $-4°$ and $0°$ C., there are added 500 mg of a mean molecular weight heparin fraction (M.W. about 10000, code number: D-212/A), obtained by fractionation with ethanol of heparin PROQUIFIN, lot 7926-7935, said fraction having a sulfation degree ($SO_3^-/COO^-$) of 1.5 and a barium acetate electrophoretic pattern which shows a very important "fast moving" component. The mixture is left to stand 1 hour under stirring at room temperature, then it is poured into 250 ml of cold diethyl ether ($-10°$ to $4°$ C.), and afterwards treated as described in Examples 1 and 2. Thus, a depolymerized and supersulfated sodium heparin (code number: AH-17) is obtained having the following characteristics:

M.W.: 3000–5000 (formula IV, m=5–8)

Elemental analysis: S: 12.70%; C: 17.24%; H: 3.10%; N: 1.67%

Sulfation degree ($SO_3^-/COO^-$): 2.5

Figure 6:
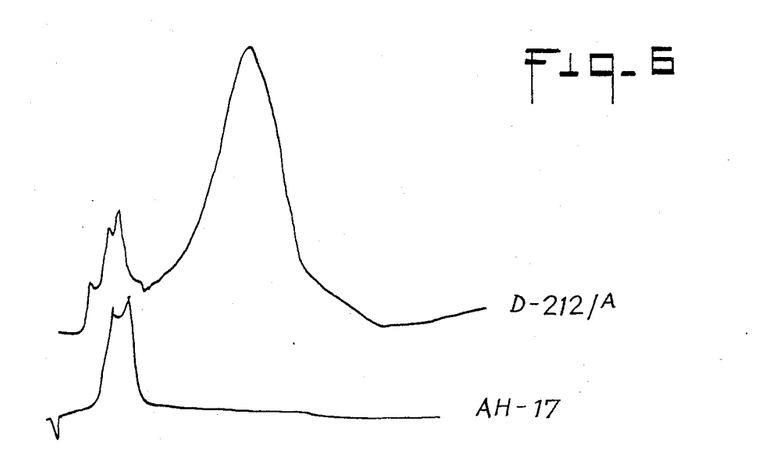

IR spectrum: broad band in the region 1300–1200 $cm^{-1}$, characteristic of the sulfate groups Barium acetate electrophoresis: FIG. 6 indicates that AH-17, compared to the starting heparin fraction, shows a "slow-moving" component only.

EXAMPLE 5

To a mixture of 20 ml of 95% sulfuric acid and 10 ml of 98% chlorosulfonic acid, cooled to a temperature between −4° and 0° C., there is added 1 g of heparin from pig intestinal mucosa (PROQUIFIN, lot 7926–7935, code number: D-212) having a sulfation degree of 1.95, then the reaction mixture is stirred 1 hour at room temperature. The mixture is poured into 500 ml of cold diethyl ether (−4° to 4° C.), the precipitate is filtered and washed with cold diethyl ether. The product thus obtained is dissolved in 0.1M calcium chloride aqueous solution, then 0.5M calcium hydroxide is added thereto up to pH 8. The solution is dialysed against 500 ml of 0.1M calcium chloride solution and then against distilled water. By slow evaporation under reduced pressure, a calcium salt of a depolymerized and supersulfated heparin is obtained as a white powder.

EXAMPLES 6 TO 10

To a mixture of 10 ml of 98% sulfuric acid and 5 ml of chlorosulfonic acid, cooled to a temperature between −4° and 0° C., there are added 500 mg of heparin from pig intestinal mucosa (PROQUIFIN, lot 7926–7935, code number: D-212) having a sulfation degree of 1.95 and a molecular weight 13,500. By operating as described in Example 1, a depolymerized and supersulfated heparin (code number: AH-104) is obtained, in 98% yield.

The same procedure and conditions are followed in 4 parallel experiments in which the same starting heparin is used. There are obtained the products designated by their code numbers AH-103, AH-105, AH-106 and AH-107. The characteristics of the products thus obtained as well as those of the product coded AH-104 are given in Table IV.

TABLE IV

| Ex. | Product | Elemental Analysis | | | | Sulfation degree | Yield by weight |
|---|---|---|---|---|---|---|---|
| | | S % | C % | H % | N % | | |
| 6 | AH-104 | 14.54 | 15.42 | 2.84 | 1.43 | 2.9 ± 0.1 | 98% |
| 7 | AH-103 | 14.63 | 15.53 | 2.76 | 1.43 | 2.8 ± 0.1 | 89% |
| 8 | AH-105 | 14.48 | 15.43 | 2.61 | 1.44 | 3.0 ± 0.1 | 67% |
| 9 | AH-106 | 14.54 | 15.53 | 2.81 | 1.46 | 2.8 ± 0.1 | 96% |
| 10 | AH-107 | 14.12 | 15.65 | 2.80 | 1.40 | 3.0 ± 0.1 | 77% |

Molecular weight: about 6000 for the 5 products

IR spectrum: the 5 products show a spectrum identical to that of compound AH-16 described in Example 1

Electrophoresis in hydrochloric acid: the electrophoretic profiles are identical to those of FIG. 1 for both the starting heparin and the 5 products Barium acetate electrophoresis: the electrophoretic profiles are identical to those of FIG. 2 for both the starting heparin and the 5 products, apart from the fact that the traces relative to the 5 products do not show the background noise—caused by a temporary defect of the tracing pen or of the paper—observed in the horizontal cart of the graph of FIG. 2 relative to AH-16

13C-NMR spectrum: the 5 products and the starting compound present the same spectra as those given in FIG. 3.

The 5 compounds thus obtained are identical each other and identical to the compound described in Example 1 as well.

EXAMPLES 11 TO 14

In 4 parallel experiments, to a mixture of 10 ml of 98% sulfuric acid and 5 ml of chlorosulfonic acid, cooled to −4°-0° C., there are added 500 mg of previously lyophilized heparin from pig intestinal mucosa (DIOSYNTH batch CH/N 665, code number: D-479), having a sulfation degree ($SO_3^-/COO^-$) of 2.1 and a molecular weight of about 11000. The reaction mixture is left to stand 1 hour at 0° C., then it is poured into 250 ml of diethyl ether previously cooled (between −10° C. and +4° C.). By operating as described in Example 1 the products of Table V are obtained.

TABLE V

| Ex. | Product | Elemental Analysis | | | | Sulfation degree | Yield by weight |
|---|---|---|---|---|---|---|---|
| | | S % | C % | H % | N % | | |
| 11 | AH-108 | 14.88 | 15.29 | 2.52 | 1.47 | 3.1 ± 0.1 | 90% |
| 12 | AH-109 | 14.43 | 15.48 | 2.72 | 1.44 | 3.0 ± 0.1 | 106% |
| 13 | AH-110 | 14.45 | 15.72 | 2.76 | 1.50 | 2.9 ± 0.1 | 65% |
| 14 | AH-111 | 14.55 | 15.08 | 2.60 | 1.41 | 3.0 ± 0.1 | 23% |

Molecular weight: about 6000 for the 4 products

Figure 7:
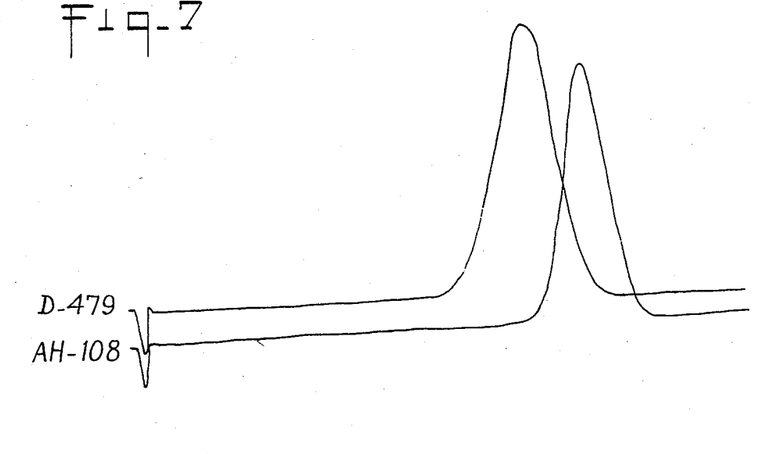
Figure 8:
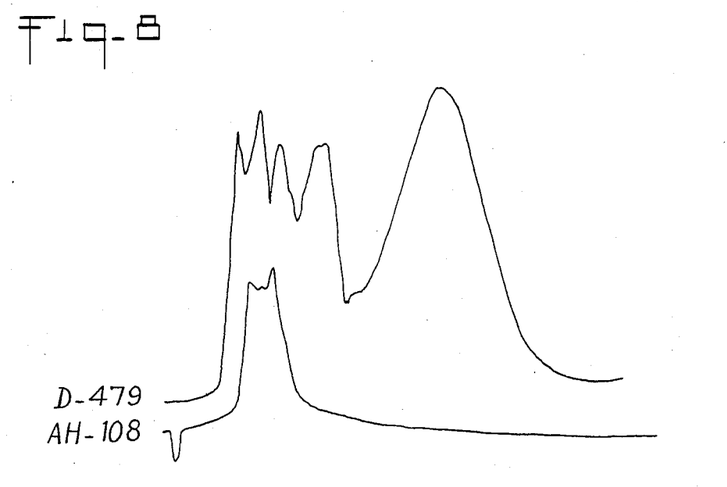

IR spectrum: broad band beween 1300 and 1200 $cm^{-1}$, characteristic of the sulfate groups Electroporesis in hydrochloric acid: FIG. 7 shows the traces of the starting heparin D-479 and of one of the 4 samples obtained in the differents experiments (AH-108). The traces of the other three compounds are identical. This figure evidences the significant increase of the electrophoretic migration of the depolymerized and supersulfated heparin in comparison with the starting heparin Barium acetate electrophoresis: FIG. 8 shows the traces of the starting heparin D-479 and of AH-108. It results that the depolymerized and supersulfated heparin has a "slow-moving" electrophoretic profile, unlike the starting heparin containing "slow-moving" components as well as "fast-moving" components. The traces of the products AH-109, AH-110 and AH-111 are identical to that of AH-108.

EXAMPLE 15

To a mixture of 10 ml of 98% sulfuric acid and 5 ml of chlorosulfonic acid, cooled to a temperature between −4° and 0° C., there are added 500 mg of heparin from pig intestinal mucosa (TERHORMON, batch 574/018, code number: D-98) having a sulfation degree of 1.8 and a molecular weight 13500. By operating as described in Example 1, a depolymerized and supersulfated heparin is obtained, in 75% yield (AH-118). The product has the following characteristics:

M.W.: about 6000

Elemental analysis: S: 13.90%; C: 15.75%; H: 2.96%; N: 1.48%

Sulfation degree ($SO_3^-/COO^-$): 2.8±0.1

Figure 9:
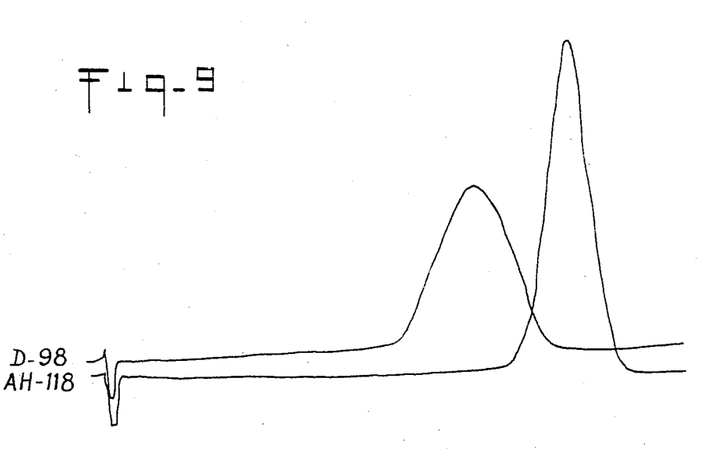

IR spectrum: broad band in the region 1300–1200 $cm^{-1}$, characteristic of the sulfate groups Electrophoresis in hydrochloric acid: FIG. 9 shows the traces of the starting heparin D-98 and of the product AH-118. A significant increase of the electrophoretic mobility of AH-118 compared with the starting heparin D-98, may be observed. FIG. 9 shows also that the compound AH-118 possesses a photodensitometric profile analogous to those of compounds AH-16 (Example 1, FIG. 1) and AH-17 (Example 4, FIG. 6) whereas the starting heparin D-98 appears very heterogeneous and completely different from the starting heparins utilized in Examples 1 and 4

Figure 10:
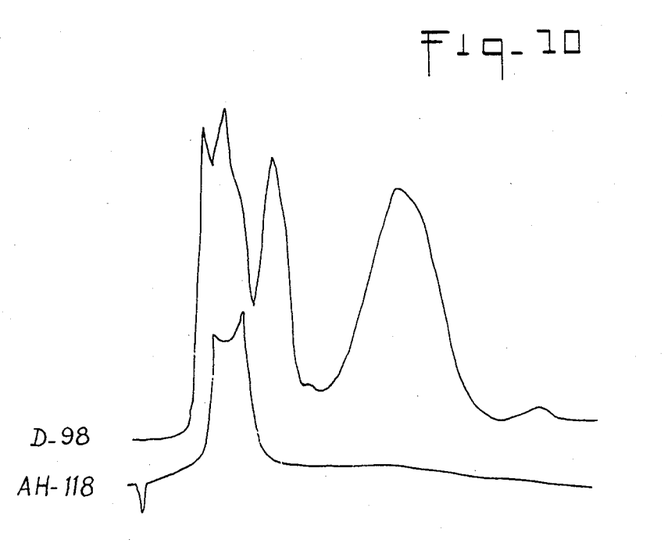

Barium acetate electrophoresis: FIG. 10 indicates that AH-118 shows a "slow-moving" electrophoretic characteristic which is different from that of the starting heparin D-98 showing both "slow-moving" and "fast-moving" components. FIG. 10 also confirms the data of FIG. 9 and moreover surprisingly shows that compound AH-118 is not significantly different from AH-108 of Example 11, thought the starting heparins are quite different.

EXAMPLES 16 TO 18

In three parallel experiments, 500 mg of heparin from pig intestinal mucosa (DIOSYNTH, batch CH/N 665, code n. D-479) having a sulfation degree ($SO_3^{--}$/$COO^-$) 2.1 and a molecular weight 11000 are added and 15 ml of a mixture of 98% sulfuric acid and 98% chlorosulfonic acid in the following ratios:

Example 16: 1:4
Example 17: 1:1
Example 18: 4:1

By operating as described in Example 1, three depolymerized and supersulfated heparins, having the characteristics given in Table VI, are obtained.

TABLE VI

| Example (code n.) | Sulfation degree | Molecular weight | Yield % by weight |
|---|---|---|---|
| 16 (AH-67) | 2.5 | 4000 | 89.9 |
| 17 (AH-65) | 2.5 | 3800 | 86.8 |
| 18 (AH-68) | 2.8 | 4500 | 77.4 |

EXAMPLE 19

To 475 ml of 98% (acidimetric titre) sulfuric acid cooled at −10° C. there is added (in 15 minutes) 237.5 ml of 98% (acidimetric titre) chlorosulfonic acid and the mixture thus obtained is stirred 30 minutes at −10° C. Then, 95 g of heparin PARKE-DAVIS (molecular weight, calculated by the electrophoretic method on polyacrylamide gel: 19200; sulfate-to-carboxyl ratio, calculated by the conductimetric method: 2.27), containing 1.7% of moisture, are added in 30 minutes under stirring at the same temperature. The reaction mixture is treated with 45 ml of 80% (v/v) sulfuric acid at −10° C. and it is allowed to reach 15° C. in about 100 minutes. The reaction mixture is then cooled at −10° C. again and poured into 4 liters of diethyl ether previously cooled at −10° C. By operating as described in Example 1, there is obtained a depolymerized, supersulfated heparin, code number DS-16, having the following characteristics molecular weight, calculated by the electrophoretic method on polyacrylamide gel: 8600;
molecular weight, calculated by integrating the anomeric signals of the 13C-NMR: 8500;
molecular weight values found by gel permeation chromatography on silica columns (6 nm and 50 nm) calibrated with xylan sulfates of known molecular weight:
number average m.w.: about 5300
weight average m.w.: about 8500;
sulfate-to-carboxyl ratio, calculated by the conductimetric method: 3.33;
13C-NMR (ratio of reducing-to-nonreducing residues): a sample of DS-16 presents characteristic signals of a low molecular weight, supersulfated heparin, significantly different from those of the starting heparin; more particularly
(a) at 100 ppm, in the anomeric region, it is observed the shift to lower fields of the signal which is attributed to the N-sulfated glucosamine,
(b) the presence of new peaks in the region of the C-1 reducing (due to terminal units) at 95.11 and 94.61 ppm,
(c) disappearance of the signal which is attributed to the 6-OH of glucosamine at 61 ppm and increase of the intensity of the signal attributed to the 6-O-sulfate group,
(d) appearance of a new peak at 59.5 ppm (which is unnoticeable in the starting heparin, see B. Casu et al., Biochem. J. 1981, 197, 599–609) indicating that most of the hydroxy groups in the 3 position of the glucosamine residue are sulfated.
Yield: 131% by weight.

The depolymerized and supersulfated heparin DS-16 has the following biological properties:
the APTT and anti-Xa activities, ex-vivo in rats, are 10% and 60%, respectively, as compared with unmodified heparin, with an anti-Xa/APTT ratio higher than 3;
the antithrombotic activity (venous stasis model, in rats) is comparable to that of the starting heparin, with no significant prolongation of bleeding time;
the lipasemic (lipoproteinlipase-releasing) activity is more than twice as that of heparin.

It has surprisingly been found that DS-16 has a high lipasemic activity even after intraduodenal administration: after administration of 400 mg/kg i.d. in rats, a 70% release of lipoproteinlipase is observed (controls: 9%) whilst heparin is inactive by intraduodenal route.

EXAMPLE 20

To 20 ml of 98% sulfuric acid cooled at −10° C. there is added 10 ml of chlorosulfonic acid and 4 g of the same heparin used as starting material of the Example 1, containing 1.7% of moisture, are added to the acid mixture at −5° C. When the heparin is well dispersed in the medium, 1.5 ml of 80% (v/v) sulfuric acid is added in 10 minutes, then the mixture is allowed to stand 1 hour at 0° C. and 1 hour at room temperature and finally poured into 200 ml of diethyl ether previously cooled at −10° C. The precipitate thus obtained is filtered, washed with diethyl ether and treated with a saturated sodium hydrogen carbonate solution until neutrality. There is obtained a depolymerized, supersulfated heparin having a sulfation degree of 3.0±0.1 and containing 45% of a population of molecules having a molecular weight lower than 5000 and the remaining 55% of a population of molecules having a molecular weight between 5000 and 10,000. Yield: 129.6% by weight.

EXAMPLE 21

The same procedure described in Example 20, in which 3 ml of 80% (v/v) sulfuric acid are added in 30 minutes, instead of 1.5 ml in 10 minutes, gives a depolymerized, supersulfated heparin containing 70% of a population of molecules having a molecular weight lower than 5000 and the remaining 30% of a population of molecules having a molecular weight between 5000 and 10,000. Sulfation degree: 3.0±1; yield 128.75% by weight.

EXAMPLE 22

The procedure of Examples 16 to 18 has been reproduced by using 15 ml of sulfuric acid 98% alone, 15 ml of a mixture of 98% sulfuric acid and of 98% of chlorosulfonic acid in the ratio 1:2 and 15 ml of chlorosulfonic acid alone, respectively. The products thus obtained have been given the codes AH-63, AH-66 and AH-64, respectively. Samples of these products as well as of the products of Examples 16 to 18 have been examined in the barium acetate electrophoresis and their electropherograms have been compared with those of the products of Examples 1 (AH-16, FIG. 1), 2 (AH-18, FIG. 4), 3 (AH-19, FIG. 5), 4 (AH-17, FIG. 2), 11 (AH-108, FIG. 8) and 15 (AH-118, FIG. 10) which are all almost identical.

The comparison of these electropherograms gave the following results:

(a) The product AH-63 (sulfuric acid alone, ratio 1:0), obtained a very low yield together with a lot of carbonized material, shows an inversion of the ratio "fast moving" to "slow moving" components demonstrating a very extensive degradation of the starting heparin and the obtention of a mixture of oligosaccharides.

(b) The products
AH-68 (ratio 4:1)
AH-65 (ratio 1:1)
AH-66 (ratio 1:2)
AH-67 (ratio 1:4)
show electrophoretic patterns similar to those of the products obtained with a sulfuric acid-to-chlorosulfonic ratio of 2:1. However AH-68 shows the appearance of a feeble signal of "fast moving" species demostrating that the ratio 4:1 is the maximum one allowing a good performance of the process of the present invention. On the contrary, it is assumed that a ratio lower than 1:4 could give some good results.

(c) The product AH-64 (chlorosulfonic acid alone), obtained in a low yield, shows a very complex electropherogram, indicative of multiple species, which is practically impossible to explain. In any case, it is completely different from that of the products obtained according to the process of the present invention.

EXAMPLE 23

Treatment of a heparin with chlorosulfonic acid in pyridine.

(a) To a mixture of 1 g of heparin from pig intestinal mucosa (PROQUIFIN, lot 7926-7935, code number: D-212) in 20 ml of the pyridine, cooled with a carbon dioxide/acetone mixture there is added 5 ml of chlorosulfonic acid. The homogeneous mixture is then heated 1 hour at 65° C. The mixture is allowed to stand 2 hours at the same temperature without stirring, then it is cooled and heated with methanol in order to complete the precipitation. The precipitate thus obtained is filtered, and washed with methanol and diethyl ether. There is obtained 500 mg of a product which, in the barium acetate electrophoresis, shows the same electropherogram as the starting heparin.

(b) An amount of 1 g of heparin from pig intestinal mucosa (PROQUIFIN, lot 7926-7935, code number: D-212) having a sulfation degree of 1.95, previously dried on $P_2O_5$ under reduced pressure, is added to a mixture of 30 ml of anhydrous pyridine and 2.5 ml of chlorosulfonic acid on an ice bath. The reaction mixture is then heated 6 hours at 60°-65° C. under stirring in the absence of moisture, then it is allowed to reach the room temperature. The mixture is poured into ice water and its pH is adjusted to 7.5, then extracted three times with chloroform. The aqueous solution is concentrated to 50 ml and dialysed against deionized water using a membrane at 3500 D (THOMAS DIALYZER TUBING 3787-H47). By concentration under reduced pressure, there is obtained 0.9 g of a product having a sulfate-to-carboxyl ratio of about 1.9. Spectral analysis shows that it is not significantly different from the starting heparin.

Even though the specification and claims recite a molecular weight of from 2000 to 9000, a depolymerized and supersulfated heparin according to the present invention might include a minor amount of supersulfated species having a molecular weight higher than 9000, generally up to 10000, as described in Examples 20 and 21, but the presence of such a minor amount or larger molecules does not change the average molecular weight between 2000 and 9000 nor the pharmacological properties of the product substantially.

We claim:

1. A depolymerized and supersulfated heparin having a molecular weight between 2000 and 9000 and a sulfation degree of at least 2.5, represented by the following formula wherein A represents H and $SO_3^-$, B represents $SO_3^-$ and $COCH_3$ and m is an integer from 4 to 15; or a pharmaceutically acceptable salt thereof.

2. A depolymerized and supersulfated heparin as claimed in claim 1, in form of its sodium salt.

3. A depolymerized and supersulfated heparin as claimed in claim 1, in form of its calcium salt.

4. A depolymerized and supersulfated heparin having the formula as in claim 1, wherein
m is as defined in claim 1
B is a $COCH_3$ group in 0 to about 30% of the m disaccharide units, according to the percent of acetyl group existing in the commercial heparin from which the supersulfated heparin derives, and a $SO_3^-$ group in the remaining disaccharide units;
the substituent A in the position 3 of the glucosamine subunit is $SO_3^-$ in at least 30% of the m disaccharide units and hydrogen in the remaining ones;

the substituent A in the position 2 of the uronic acid subunit is $SO_3^-$ in at least 50% of the m disaccharide units and hydrogen in the remaining ones;

the substituent A in the position 3 of the uronic acid subunit is prevalently hydrogen, but it can be $SO_3^-$ in some of the m disaccharide units.

5. A depolymerized and supersulfated heparin having the formula as in claim 1, wherein m is as defined in claim 1

B is a $COCH_3$ group in 0 to about 30% of the m disaccharide units, according to the percent of acetyl groups existing in the commercial heparin from which the supersulfated heparin derives, and a $SO_3^-$ group in the remaining disaccharide units;

the substituent A in the position 3 of the glucosamine subunit is $SO_3^-$ in at least 50% of the m disaccharide units and hydrogen in the remaining ones;

the substituent A in the position 2 of the uronic acid subunit is $SO_3^-$ in at least 70% of the m disaccharide units and hydrogen in the remaining ones;

the substituent A in the position 3 of the uronic acid subunit is prevalently hydrogen, but it can be $SO_3^-$ in some of the m disaccharide units.

6. A depolymerized and supersulfated having a molecular weight between 2000 and 9000 and a sulfation degree of at least 2.5, characterized by the dominating structure 7. A depolymerized and supersulfated heparin according to claim 6, having a sulfation degree of at least $2.8 \pm 0.1$.

8. A depolymerized and supersulfated heparin according to claim 6, having a sulfation degree of from $3.0 \pm 0.1$ to $3.3 \pm 0.1$ 9. A process for the preparation of a heparin as claimed in claims 1, 2 or 3, in which a heparin of natural origin or a fraction thereof is treated with a mixture of sulfuric acid and chlorosulfonic acid in a ratio sulfuric acid:chlorosulfonic acid of from 1:4 to 4:1 and at a concentration of said acids of at least 95% by weight, at a temperature of from $-20°$ to $40°$ C. and the product thus obtained is isolated as an alkali metal salt thereof or converted into a pharmaceutically acceptable salt thereof.

10. A process as claimed in claim 9, in which the ratio sulfuric acid:cholorsulfonic acid is about 2:1.

11. A process as claimed in claim 9 in which the depolymerized and supersulfated heparin is isolated as sodium salt.

12. A process as claimed in claim 9 in which the depolymerized and supersulfated heparin obtained has a sulfation degree at least 20% higher than that of the starting heparin or fraction thereof.

13. A process as claimed in claim 9 in which heparin is added to the acids mixture at a temperature lower than $-3°$ C., and the reaction is carried out for about one hour at less than $-3°$ C. and about one hour at room temperature.

14. A process as claimed in claim 9 in which diluted sulfuric acid, in an amount of from about 0.2 to about 1.5 g of sulfuric acid per gram of starting heparin, is added to the reaction mixture.

15. A process as claimed in claim 14 in which said sulfuric acid is at a dilution of 70–85%.

16. A pharmaceutical composition having potential antithrombotic action and hypolipemic and fibrinolytic activity in dosage unit form comprising from 1 to 1500 mg of a depolymerized and supersulfated heparin as claimed in one of claims 1 to 3 in admixture with a pharmaceutical carrier.

17. A pharmaceutical composition for the treatment of atherosclerosis and the prevention for thrombosis, comprising, as active ingredient, a depolymerized and supersulfated heparin as claimed in one of claims 1 to 3.

* * * * *